(12) United States Patent
Morita et al.

(10) Patent No.: US 8,258,146 B2
(45) Date of Patent: Sep. 4, 2012

(54) MINOXIDIL AQUEOUS COMPOSITION CONTAINING BILE ACID

(75) Inventors: Ritsuko Morita, Ashigarakami-gun (JP); Katsuhiko Kanazawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 219 days.

(21) Appl. No.: 12/728,915

(22) Filed: Mar. 22, 2010

(65) Prior Publication Data

US 2010/0240684 A1  Sep. 23, 2010

(30) Foreign Application Priority Data

Mar. 23, 2009 (JP) ................ 2009-069887

(51) Int. Cl.
*A61K 31/506* (2006.01)
*C07J 9/00* (2006.01)

(52) U.S. Cl. ......... 514/272; 514/275; 552/553; 552/555

(58) Field of Classification Search .............. 514/272, 514/275; 552/553, 555
See application file for complete search history.

(56) References Cited

U.S. PATENT DOCUMENTS

| | | | |
|---|---|---|---|
| 3,461,461 A | 8/1969 | Anthony et al. | |
| 4,139,619 A | 2/1979 | Chidsey, III | |
| 4,185,099 A * | 1/1980 | Sorbini | 514/171 |
| 4,596,812 A | 6/1986 | Chidsey, III et al. | |
| 5,183,817 A * | 2/1993 | Bazzano | 514/256 |
| 7,442,369 B1 * | 10/2008 | Pena et al. | 424/70.1 |
| 2002/0031558 A1 | 3/2002 | Yoo | |

FOREIGN PATENT DOCUMENTS

| | | |
|---|---|---|
| JP | 01-174355 A | 7/1989 |
| JP | 2004-059587 A | 2/2004 |
| JP | 2006-176447 A | 7/2006 |
| WO | 99/53923 A1 | 10/1999 |
| WO | 2006/057637 A1 | 6/2006 |
| WO | 2007/074476 A1 | 7/2007 |

OTHER PUBLICATIONS

Extended European Search Report corresponding to EP Application No./Patent No. 10003003.0-2112, dated Jun. 24, 2010.

* cited by examiner

*Primary Examiner* — Jennifer M Kim

(74) *Attorney, Agent, or Firm* — Sughrue Mion, PLLC

(57) ABSTRACT

An object of the present invention is to provide a liquid composition wherein minoxidil can be dissolved at a relatively high concentration (the saturating amount or above), stimulation of skin and stickiness is suppressed without containing an organic solvent, and excellent effects of percutaneous absorption is achieved. The present invention provides a liquid composition comprising (i) minoxidil, (ii) bile acid or a salt thereof, and (iii) an aqueous medium in an amount of 30% by weight or more of the weight of the composition.

6 Claims, 1 Drawing Sheet

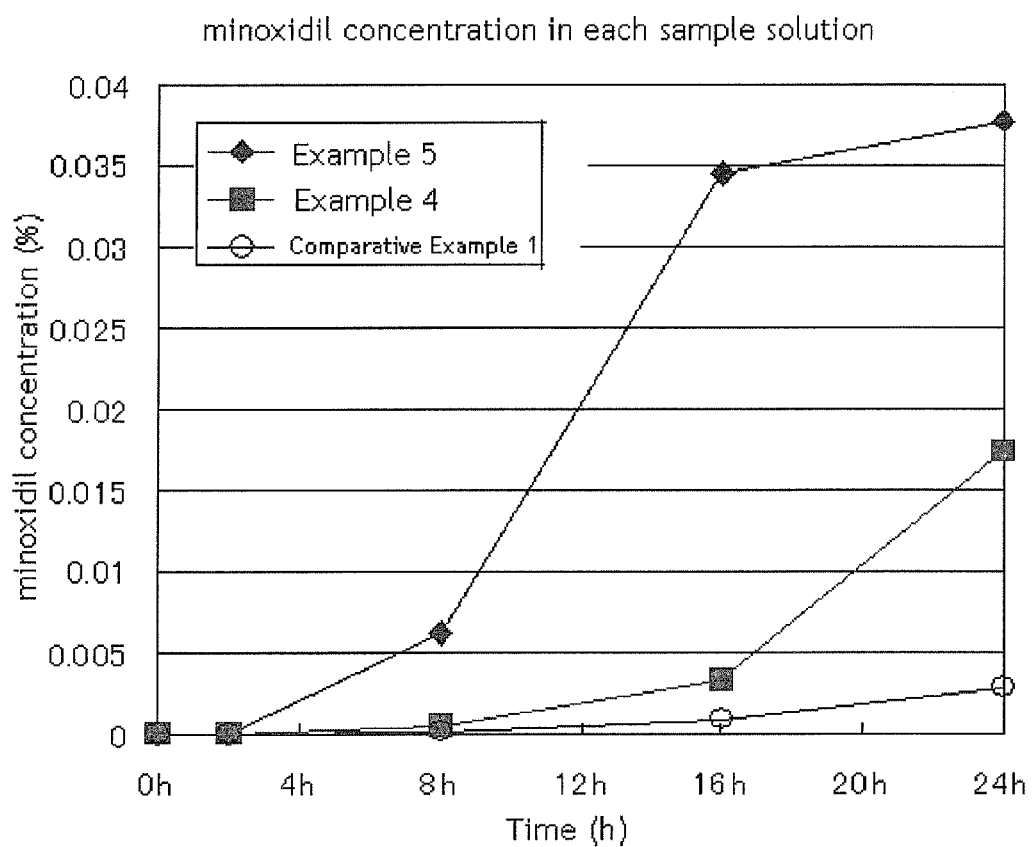

ated from the group consisting of deoxycholic acid, ursodeoxycholic acid, cholic acid, ketocholic acid, lithocholic acid, hyodeoxycholic acid, glycocholic acid, taurocholic acid, chenodeoxycholic acid, hyocholic acid, and 5α-cyprinol.

MINOXIDIL AQUEOUS COMPOSITION CONTAINING BILE ACID

TECHNICAL FIELD

The present invention relates to an aqueous composition (a liquid preparation) containing highly concentrated minoxidil.

BACKGROUND ART

Minoxidil (i.e., 2,4-diamino-6-piperidinyl-pyrimidine-3-oxide) is an active ingredient of Loniten (registered trademark) and Rogaine (registered trademark), and it is commercially available from Pharmacia and Upjohn for treatment of hypertension and for treatment and prevention of androgenic alopecia (male pattern baldness and female pattern baldness). A method for preparing minoxidil and use thereof for an antihypertensive agent are disclosed in U.S. Pat. No. 3,461,461. A method for use of the compound to grow hair and to treat male pattern baldness and female pattern baldness and a topical preparation therefor are disclosed in U.S. Pat. Nos. 4,139,619 and 4,596,812.

A pharmaceutical composition for topical application, such as Rogaine (registered trademark), can be in various forms, such as a solution, gel or suspension. When a composition for topical application is a solution or gel; i.e., when an active ingredient such as minoxidil is dissolved in a carrier solution, in general, absorption can be improved, as compared with a composition for topical application in the form of a suspension; i.e., a case where a composition comprising an active ingredient is suspended in the composition.

Minoxidil is poorly soluble in water. When it is dissolved in an aqueous solvent, 50% or more of the solution is generally composed of ethanol (e.g., JP Patent Publication (kokai) No. 2004-59587 A), and adverse effects resulting therefrom (e.g., stimulation of the scalp and deteriorated sense of use, such as stickiness, due to increased solvent amount) are issues of concern. JP Patent Publication (kokai) No. 2006-176447 A discloses a composition that yields reduced stimulation of the scalp caused by ethanol; however, the ethanol content is 40% or more and the problem of stimulation is not fundamentally resolved. Thus, improvement in solubility and absorption of minoxidil still depends on percutaneous absorption that is carried out in a concentration-gradient manner by elevating the concentration of minoxidil to be dissolved with the aid of an organic solvent. There was no means for improving absorption efficiency without the use of an organic solvent.

The term "bile acid" is a generic term for compounds that are steroid derivatives which are contained in bile generated and absorbed in vivo and have cholane skeleton. Bile acid is occasionally used as a solubilizer at the industrial level. Specifically, ursodeoxycholic acid is used as a choleretic drug, and deoxycholic acid is used as a dispersant for a pharmaceutical additive, although its remarkable effects for solubilizing minoxidil were not known in the past. Also, JP Patent Publication (kokai) No. H1-174355 A (1989) discloses that mixing of monoacylglycerophospholipid, fatty acid monoglyceride, and bile acid would double the percutaneous absorption efficiency of indomethacin. However, such doubling was not achieved solely by bile acid, and effects of accelerating percutaneous absorption by bile acid alone were not known.

SUMMARY OF THE INVENTION

An object of the present invention is to overcome drawbacks of the prior art techniques described above. Specifically, an object of the present invention is to provide a liquid composition wherein minoxidil can be dissolved at a relatively high concentration (the saturating amount or above), stimulation of skin and stickiness is suppressed without containing an organic solvent, and excellent effects of percutaneous absorption is achieved.

The present inventors have conducted concentrated studies in order to attain the above object. As a result, they discovered that bile acid would exhibit remarkable effects as aminoxidil solubilizer and as a percutaneous absorption accelerator, thereby completing the present invention.

The present invention provides a liquid composition comprising (i) minoxidil, (ii) bile acid or a salt thereof, and (iii) an aqueous medium in an amount of 30% by weight or more of the weight of the composition.

Preferably, minoxidil content is 0.2% to 5% by weight relative to the weight of the composition.

Preferably, the bile acid is at least one which is selected from the group consisting of deoxycholic acid, ursodeoxycholic acid, cholic acid, ketocholic acid, lithocholic acid, hyodeoxycholic acid, glycocholic acid, taurocholic acid, chenodeoxycholic acid, hyocholic acid, and 5α-cyprinol, or a salt of any thereof.

Preferably, the bile acid is deoxycholic acid, ursodeoxycholic acid, or a salt thereof.

Preferably, bile acid content is 0.01% to 20% by weight relative to the weight of the composition.

Preferably, the liquid composition of the present invention further comprises (iv) at least one which is selected from the group consisting of gelatin, acid-treated gelatin, casein, globulin, fibroin, fibrinogen, keratin, ferritin, laminin, fibronectin, and vitronectin, or a salt of any thereof.

Preferably, the liquid composition of the present invention further comprises (iv) casein or gelatin.

Preferably, the liquid composition of the present invention further comprises (iv) at least one which is selected from the group consisting of lipoprotein, glycoprotein, phosphoprotein, hemoprotein, flavoprotein, and metalloprotein.

The present invention further provides aminoxidil solubilizer which comprises at least 1 type of bile acid which is selected from the group consisting of deoxycholic acid, ursodeoxycholic acid, cholic acid, ketocholic acid, lithocholic acid, hyodeoxycholic acid, glycocholic acid, taurocholic acid, chenodeoxycholic acid, hyocholic acid, and 5α-cyprinol.

The present invention further provides a percutaneous absorption accelerator for minoxidil which comprises at least 1 type of bile acid which is selected from the group consisting of deoxycholic acid, ursodeoxycholic acid, cholic acid, ketocholic acid, lithocholic acid, hyodeoxycholic acid, glycocholic acid, taurocholic acid, chenodeoxycholic acid, hyocholic acid, and 5α-cyprinol.

The liquid composition of the present invention contains minoxidil at a relatively high concentration (a saturating amount or above), produces suppressed stimulation of skin and stickiness, and produces excellent effects of percutaneous absorption.

BRIEF DESCRIPTION OF THE DRAWING

FIG. 1 shows the results of a skin permeability test on hairless rats with the use of dispersions of Example 4 and Example 5 and an ethanol-containing 1% minoxidil preparation of Comparative Example 1.

EMBODIMENTS FOR CARRYING OUT THE INVENTION

Hereafter, embodiments of the present invention are described in greater detail.

The liquid composition of the present invention comprises 0.2% by weight or more minoxidil which is stably dissolved therein. Minoxidil is a compound represented by a generic term: 2,4-diamino-6-diamino-6-piperidino-pyrimidine-3-oxide, which is used as a therapeutic agent for hypertension. Hair growth functions thereof were found later and this compound has drawn attention recent years. The term "stably dissolved" used herein refers to a condition that no precipitation is visually observed after 1-week-storage at 40° C.

The surprising effects that were discovered by the present invention are such that bile acid can function as aminoxidil solubilizer and, further, as a percutaneous absorption accelerator for minoxidil. Synthesized or extracted bile acid may be used, without particular limitation.

Specific examples of bile acids include deoxycholic acid, ursodeoxycholic acid, cholic acid, ketocholic acid, lithocholic acid, hyodeoxycholic acid, glycocholic acid, taurocholic acid, chenodeoxycholic acid, hyocholic acid, 5α-cyprinol, and a salt of any thereof, with ursodeoxycholic acid, deoxycholic acid, or a salt of any thereof being preferable.

When bile acid is used, synthesized or extracted bile acid may be used, and its origin is not particularly limited. For example, bile acid obtained from a pig, cattle, goat, bear, human, or bird or bile acid obtained via gene recombination may be used.

The liquid composition of the present invention preferably contains 0.01% to 20% bile acid by weight, and it more preferably contains 0.01% to 100% minoxidil by weight relative to the weight of bile acid.

Minoxidil content in the liquid composition of the present invention is preferably 0.2% to 5% by weight, more preferably 0.2% to 4% by weight, further preferably 0.2% to 3% by weight, and most preferably 0.2% to 1.0% by weight.

Further, the liquid composition of the present invention preferably contains a multimeric or conjugate protein. A multimeric or conjugate protein is preferably biocompatible from the viewpoint of safety and performance.

Specific examples of multimeric proteins include gelatin, acid-treated gelatin, casein, globulin, fibroin, fibrinogen, keratin, ferritin, laminin, fibronectin, and vitronectin, with gelatin being preferable.

Specific examples of conjugate proteins include lipoprotein, glycoprotein, phosphoprotein, hemoprotein, flavoprotein, and metalloprotein. Specific examples of glycoproteins include immunoglobulin transferrin, fibrinogen, and proteoglycan. Specific examples of phosphoproteins include casein and sodium caseinate. A specific example of hemoprotein is hemoglobin. A specific example of lipoprotein is β-lipoprotein in the blood. A protein of any origin, a chemically modified protein, or a chemically denatured protein may be used without limitation.

Among the aforementioned proteins, casein or gelatin is most preferable. When casein is used in the present invention, the origin of casein is not particularly limited. It may be derived from milk or bean, and α-casein, β-casein, γ-casein, κ-casein, or a mixture of any thereof can be used. Casein can be used alone or in combinations of two or more. When gelatin is used, the origin of gelatin is not particularly limited, and gelatin derived from fish, cattle, pig, or goat or gene recombinant gelatin may be used.

In the present invention, a multimeric or conjugate protein can be used alone or in combinations of two or more.

The liquid composition of the present invention preferably comprises a multimeric or conjugate protein in an amount of 0.2% to 15% by weight, and more preferably 0.4% to 5% by weight.

The liquid composition of the present invention further preferably comprises minoxidil in an amount of 0.1% to 200% by weight relative to the weight of the protein.

Safety of biocompatible polymers, including casein and gelatin, for human bodies has been verified. Thus, improvement can be expected in safety in addition to performance as a solubilizer.

Examples of aqueous medium that can be used in the present invention include an aqueous solution of an organic acid, an organic base, an inorganic acid, an inorganic base, and buffer. Aqueous medium content in the liquid composition of the present invention is 30% by weight or more, preferably 50% by weight or more, more preferably 70% by weight or more, and most preferably 99% by weight or more. Preferably, the liquid composition is substantially free of an organic solvent, such as ethanol, propylene glycol, dipropylene glycol, 1,3-butylene glycol, pentylene glycol, or dipentylene glycol.

Specific examples of an organic acids, organic bases, inorganic acids, or inorganic bases include, but are not limited to: aqueous solutions of organic acids such as citric acid, ascorbic acid, gluconic acid, carboxylic acid, tartaric acid, succinic acid, acetic acid, phthalic acid, trifluoroacetic acid, morpholinoethanesulfonic acid, and 2-[4-(2-hydroxyethyl)-1-piperazinyl]ethanesulfonic acid; aqueous solutions of organic bases such as tris(hydroxymethyl), aminomethane, and ammonia; aqueous solutions of inorganic acids such as hydrochloric acid, perchloric acid, and carbonic acid; and aqueous solutions of inorganic bases such as sodium phosphate, potassium phosphate, calcium hydroxide, sodium hydroxide, potassium hydroxide, and magnesium hydroxide.

In the present invention, preferably, minoxidil is dissolved at a desired concentration or higher at a low pH level, it is mixed in that state with a solution containing bile acid and other ingredients according to need, and then the pH level is adjusted with the use of the aqueous solution of an organic acid, an organic base, an inorganic acid, or an inorganic base. The pH level of the liquid composition of the present invention is preferably 8 or higher (i.e., between 8 and 12), and more preferably between 10 and 12. Such pH range is preferable since the composition may undergo hydrolysis or handling thereof may involve risk, if the pH level is excessively high.

The liquid composition of the present invention is administered percutaneously or transmucosally, for example.

Physiologically active ingredients other than minoxidil that are used in the present invention are not particularly limited, provided that such substances are absorbed through skin and exhibit activity. For example, such ingredients can be selected from among cosmetic ingredients, quasi drug ingredients, and drug ingredients. Examples include moisturizing agents, skin-lightening agents, baldness remedies, hair growth stimulants, hair growing agents, blood circulation accelerators, anti-hair graying agents, anti-aging agents, antioxidants, accelerators of collagen synthesis, anti-wrinkle agents, anti-acne agents, vitamin preparations, ultraviolet absorbers, aroma chemicals, coloring agents, anhidrotic agents, cooling agents, calefacients, inhibitors for melanin generation, melanocyte-activating agents, antibiotics, antitumor agents, antiinflammatory agents, antiallergic agents, hormone preparations, antithrombotic agents, immunosuppressive agents, therapeutic agents for skin disease, antifungal agents, nucleic acid medicine, anesthetic agents, antipyretic agents, analgesics, antipruritic agents, antihydropic agents, sedative-hypnotic agents, antianxiety agents, stimulants, psychoneurotic agents, muscle relaxants, antidepressants, combination cold remedies, therapeutic agents for diseases of the autonomic nervous system, anticonvulsive agents, sweating agents, antiperspirants, cardiotonic agents, therapeutic agents for arrhythmia, antiarrhythmic agents, vasoconstrictive agents, vasodilators, antihypertensive agents, therapeutic agents for diabetes, therapeutic agents for hyperlipidemia, respiratory stimulants, antitussive drugs, vitamin preparations, therapeutic agents for parasitic skin disease, therapeutic agents for homeostatic function, polypeptides, hormones, inhibitors of incomplete keratinization, vaccines, and skin softeners. Such physiologically active ingredients may be used alone or in combinations of two or more.

The aqueous composition containing minoxidil of the present invention can further comprise additives. Additives are not particularly limited, and one or more additives selected from the group consisting of a moisturizing agent, a softening agent, a percutaneous absorption accelerator, a soothing agent, an antiseptic agent, an antioxidant, a coloring agent, a thickener, an aroma chemical, and a pH regulator can be used.

The present invention is described in greater detail with reference to the following examples, although the technical scope of the present invention is not limited thereto.

EXAMPLE

Example 1

Deoxycholic acid (1.15 g, Wako Pure Chemical Industries, Ltd.) was dissolved in 4 ml of an aqueous solution of 1N NaOH. 2.0 ml of 50 mM trisodium citrate (pH 10) was added thereto, and the amount of the solution was brought to 14 ml with the addition of Milli-Q water. Thereafter, an aqueous solution of 2% minoxidil by weight (150 mM HCl) was added, the pH level was adjusted to 8.5 with the aid of NaOH/HCl, the volume was brought to 20 ml, and a dispersion of 0.6% minoxidil by weight (final concentration) was obtained.

Example 2

Deoxycholic acid (0.58 g, Wako Pure Chemical Industries, Ltd.) was dissolved in 2.5 ml of an aqueous solution of 1N NaOH. 2.0 ml of 50 mM trisodium citrate (pH 10) was added thereto, 2 ml of an aqueous solution of casein sodium (50 mM trisodium citrate), which had been diluted to 10% by weight in advance, was added, and the amount of the solution was brought to 14 ml with the addition of Milli-Q water. Thereafter, an aqueous solution of 2% minoxidil by weight (150 mM HCl) was added, the pH level was adjusted to 8.5 with the aid of NaOH/HCl, the volume was brought to 20 ml, and a dispersion of 0.6% minoxidil by weight (final concentration) was obtained. After the solution had been stored at 40° C. for a week, it remained transparent and stably dispersed.

Example 3

Cholic acid (1.8 g, Wako Pure Chemical Industries, Ltd.) was dissolved in 5 ml of an aqueous solution of 1N NaOH. 3.0 ml of 50 mM trisodium citrate (pH 10) was added thereto, and 2 ml of an aqueous solution of casein sodium (50 mM trisodium citrate), which had been diluted to 10% by weight in advance, was added. Thereafter, an aqueous solution of 2% minoxidil by weight (150 mM HCl) was added, the pH level was adjusted to 8.5 with the aid of NaOH/HCl, the volume was brought to 20 ml, and a dispersion of 1.0% minoxidil by weight (final concentration) was obtained. After the solution had been stored at 40° C. for a week, it remained transparent and stably dispersed.

Example 4

Ursodeoxycholic acid (0.92 g, Wako Pure Chemical Industries, Ltd.) was dissolved in 5 ml of an aqueous solution of 1N NaOH. 2.0 ml of 50 mM trisodium citrate (pH 10) was added thereto, and 2 ml of an aqueous solution of casein sodium (50 mM trisodium citrate), which had been diluted to 10% by weight in advance, was added. Thereafter, an aqueous solution of 2% minoxidil by weight (150 mM HCl) was added, the pH level was adjusted to 8.5 with the aid of NaOH/HCl, the volume was brought to 20 ml, and a dispersion of 1.0% minoxidil by weight (final concentration) was obtained. After the solution had been stored at 40° C. for a week, it remained transparent and stably dispersed.

Example 5

Deoxycholic acid (0.74 g, Wako Pure Chemical Industries, Ltd.) was dissolved in 3.4 ml of an aqueous solution of 1N NaOH. 4.5 ml of Milli-Q water was added thereto to obtain a solution, and 2 ml of an aqueous solution of casein sodium (50 mM trisodium citrate), which had been diluted to 10% by weight in advance, was added. Thereafter, an aqueous solution of 2% minoxidil by weight (150 mM HCl) was added, the pH level was adjusted to 8.5 with the aid of NaOH/HCl, the volume was brought to 20 ml, and a dispersion of 1.0% minoxidil by weight (final concentration) was obtained. After the solution had been stored at 40° C. for a week, it remained transparent and stably dispersed.

Example 6

Deoxycholic acid (1.92 g, Wako Pure Chemical Industries, Ltd.) was dissolved in 6.3 ml of an aqueous solution of 1N NaOH. 1.7 ml of Milli-Q water was added thereto to obtain a solution, and 2 ml of an aqueous solution of casein sodium (50 mM trisodium citrate), which had been diluted to 10% by weight in advance, was added. Thereafter, an aqueous solution of 2% minoxidil by weight (150 mM HCl) was added, the pH level was adjusted to 8.5 with the aid of NaOH/HCl, the volume was brought to 20 ml, and a dispersion of 1.0% minoxidil by weight (final concentration) was obtained. After the solution had been stored at 40° C. for a week, it remained transparent and stably dispersed.

Test Example 1

The dispersions of Example 4 and Example 5 and a 1% minoxidil preparation containing ethanol (RiUP, Taisho Pharmaceutical Co. Ltd., Comparative Example 1) were used in a skin permeability test on hairless rats using Franz cells. PBS (200 mM, 32±2° C.) was used as a receptor solution. 1 ml each of the samples was applied dropwise to the epidermis of each hairless rat, and the adipose of each hairless rat was filled with the receptor solution, followed by agitation. The receptor solution was withdrawn at predetermined time intervals, and the obtained solution was subjected to HPLC to measure the concentration of minoxidil that had permeated the skin. The results are shown in Table 1 and FIG. 1.

TABLE 1

|  | 0 hours | 2 hours | 8 hours | 16 hours | 24 hours |
|---|---|---|---|---|---|
| Comparative Example 1 | 0.0000% | 0.0000% | 0.0002% | 0.0009% | 0.0028% |

TABLE 1-continued

|  | 0 hours | 2 hours | 8 hours | 16 hours | 24 hours |
|---|---|---|---|---|---|
| Example 4 | 0.0000% | 0.0000% | 0.0004% | 0.0032% | 0.0174% |
| Example 5 | 0.0000% | 0.0000% | 0.0062% | 0.0345% | 0.0378% |

The results demonstrate that the amount of minoxidil that had permeated the skin in Example 4 was 6.2 times higher than that in Comparative Example 1, and that in Example 5 was 13.5 times higher than that in Comparative Example 1, when equal amounts of minoxidil were administered.

Test Example 2

Five monitors were subjected to evaluation of sense of use of the dispersions of Example 4 and Example 5 and the preparation of Comparative Example 1. As a result, the preparation of Comparative Example 1 was evaluated to leave stickiness on hands or hair after use. In contrast, the dispersions of Example 4 and Example 5 were evaluated as providing a good sense of use (i.e., the dispersions were evaluated to be excellent in providing a refreshing feeling and to be free of stickiness).

The above results verified that the aqueous preparation containing no solvent such as ethanol according to the present invention is capable of maintaining the solubility of minoxidil and improving absorption efficiency.

The invention claimed is:

1. A liquid composition comprising:
   (i) minoxidil;
   (ii) a bile acid or a salt thereof; and
   (iii) an aqueous medium in an amount of 30% by weight or more of the weight of the composition, wherein
   the liquid composition is free of an organic solvent, and
   the bile acid or salt thereof is at least one selected from the group consisting of deoxycholic acid, cholic acid, ursodeoxycholic acid, and a salt of any thereof.

2. The liquid composition according to claim 1, wherein the minoxidil content is 0.2% to 5% by weight relative to the weight of the composition.

3. The liquid composition according to claim 1, wherein the bile acid content is 0.01% to 20% by weight relative to the weight of the composition.

4. The liquid composition according to claim 1, which further comprises (iv) at least one which is selected from the group consisting of gelatin, acid-treated gelatin, casein, globulin, fibroin, fibrinogen, keratin, ferritin, laminin, fibronectin, and vitronectin, or a salt of any thereof.

5. The liquid composition according to claim 1, which further comprises (iv) casein or gelatin.

6. The liquid composition according to claim 1, which further comprises (iv) at least one which is selected from the group consisting of lipoprotein, glycoprotein, phosphoprotein, hemoprotein, flavoprotein, and metalloprotein.

* * * * *